United States Patent [19]
Feiertag et al.

[11] Patent Number: 5,793,469
[45] Date of Patent: Aug. 11, 1998

[54] VARIABLE DISTANCE, VARIABLE TEST OBJECT SIGHT TESTING APPARATUS

[75] Inventors: Carsten Feiertag, Hungen; Rainer Kirchhübel, Asslar, both of Germany

[73] Assignee: Oculus Optikgeraete GmbH, Wetzlar-Dutenhofen, Germany

[21] Appl. No.: 588,405

[22] Filed: Jan. 18, 1996

[30] Foreign Application Priority Data

Jan. 19, 1995 [DE] Germany ............ 195 01 415.4

[51] Int. Cl.$^6$ ........................................ A61B 5/14
[52] U.S. Cl. ................................ 351/221; 351/211
[58] Field of Search .................... 351/243, 214, 351/221, 211, 205, 246, 220

[56] References Cited

U.S. PATENT DOCUMENTS

| | | |
|---|---|---|
| 4,155,632 | 5/1979 | Wolbarsht . |
| 4,529,280 | 7/1985 | Nohda . |
| 5,255,027 | 10/1993 | Reiner et al. . |

FOREIGN PATENT DOCUMENTS

| | | |
|---|---|---|
| 0 492 044 A1 | 7/1992 | European Pat. Off. . |
| 2707912 C2 | 9/1977 | Germany . |
| 3733872 A1 | 6/1988 | Germany . |

*Primary Examiner*—Hung X. Dang
*Attorney, Agent, or Firm*—Flynn, Thiel, Boutell & Tanis, P.C.

[57] ABSTRACT

Sight testing apparatus, in particular sight testing apparatus with a free through-view, for examining near-sightedness and far-sightedness and color and stereoscopic vision, can operate with test objects which are located within the focal length of an imaging device and are imaged at different distances into the eye, located at the focus of the imaging device, of a subject under test. For this purpose, the size of the image must be able to be altered. For this purpose, an optical full deflection device is provided in the beam path between the image device and the test object, deflects the beam path through 180° and is constructed so as to be displaceable.

25 Claims, 3 Drawing Sheets

VARIABLE DISTANCE, VARIABLE TEST OBJECT SIGHT TESTING APPARATUS

FIELD OF THE INVENTION

The invention relates to a sight testing apparatus, in particular a sight testing apparatus with a free through-view, having an imaging device of the virtual imaging of a test object, which is located within the focal length of the imaging device and can be imaged at different distances, into the eye, located at the focus of the imaging device, of a subject under test.

BACKGROUND OF THE RELATED ART

A sight testing apparatus of this type has already been disclosed by the European Patent Application 0 492 044 Al. In contrast to comparable devices, the placing of the eyes of the subject under test at the focus of the imaging device ensures that different positions of the test object within the focal length of the imaging device also result in different viewing distances to which the eyes adapt: a natural accommodation and convergence setting of the eyes. The field of view and the visual acuity are in this case always constant.

By means of displacing the test object from infinity to a near value corresponding to the focal length of the imaging device, it is possible to measure both short-sightedness of the subject under test from zero up to the reciprocal of the focal length and long-sightedness, if a partly transparent pivotable deflecting device is provided, which is as a rule a beam-splitting mirror.

In a first pivoting position of the beam-splitting mirror, the test object is imaged at infinity; the arrangement in this case is made such that the viewing direction of the subject under test is approximately horizontal, so that is runs, for example, through the upper part of a visual aid located at the eyes, while it passes at an inclination through the lower part of the visual aid when the beam-splitting mirror has been pivoted into a second pivoting position. The subject under test in this case maintains the position of his or her head and only alters his or her viewing direction. Such a sight testing apparatus can be implemented vary compactly and at the same time ensures a free view of the test object. It is clear that both the eyes and a visual aid (for example having continuous vision lenses) can be tested in this way.

The test object must be capable of changing its position in order to be able to carry out these measurements. For this purpose, the test field carrier of the test fields used in the case of the previously disclosed arrangement as test object can be movably placed along the optical path, the associated illumination device, composed of at least a light source, a collimator and a diffusing screen or the like, also having to be coupled to such a (linear) movement. The test field carrier is as a rule itself further capable of being driven in such a way that the test field can be changed conveniently. Both the subassemblies of the test field carrier and of the illumination device accordingly comprise many individual apparatus and, in addition, both need power cables for this power supply, so that their ability to move during the running sight test presents considerable problems.

SUMMARY OF THE INVENTION

The invention has taken as its object the configuration of a sight testing apparatus of the design described in more detail above, where the test object can be imaged significantly more simply at different distances and the alteration of this distance can be carried out conveniently during the running sight test.

According to the invention, the object is achieved in that an optical full deflection device is provided in the beam path between the imaging device and the test object, it deflects the beam path through 180° and is constructed so as to be movable in the direction of the two beam path fragments which are thus formed and parallel to each other, and the test object is constructed so as to be immovable in this direction.

In this case of such an arrangement according to the invention, only one single remaining subassembly is moved longitudinally without an electrical connection, and in the simplest case only one single component moves. On the other hand, the subassemblies of more complicated composition for the presentation and the changing of the test object and its illumination device remain fixed in the sight testing apparatus, although the test object can still be placed at different distances: in contrast to the previously known device, the optical path itself can be altered in terms of length. Since in this arrangement these are linear length changes, a very simple design in terms of apparatus is possible, as is still to be shown, which because of the low mass to be moved can in addition be operated even more simply than previously.

The sight testing apparatus according to the invention can be used in a particularly versatile manner, if a partly transparent deflecting device is provided in the beam path between the eye of the subject under test and the imaging device, can preferably be pivoted and, in the process, changes the viewing direction of the eye and can at best be locked in at least two positions pivoted with respect to each other; these are, of course, those settings of the deflecting device in which the most important examinations are undertaken and which, in the case of manual operation, can be found rapidly and reliably in this way even while running a test.

For this purpose, the deflecting device can initially be locked in such a way that the viewing direction onto the test object runs approximately horizontally, for example through the upper part of a visual aid worn by the subject under test serving as a distant viewing area. This is without doubt the most important application of the sight testing apparatus, in which the view of the subject under test is directed completely freely onto the test object. However, the deflecting device can also be locked in a position in which the viewing direction onto the test object runs inclined with respect to the horizontal, for example through the lower part of a visual aid worn by the subject under test serving as a near viewing area. In this case, the subject under test maintains his or her head position and only lowers his or her sight, in order to detect the test object. In a simple way, the deflecting device can in this case be constructed as a partly transparent flat beam-splitting mirror.

The surrounding field of the test object imaged in the eye of the subject under test can be included in the measurement if a diffuse direct light source is provided in a fixed position and the deflecting device can be pivoted in such a way that a beam path leasing through the deflecting device and not able to be deflected by the latter passes from the direct light source, together with the image of the test object, into the eye of the subject under test. In this way, the contrast between the test object and its surrounding field can be objectivized and its influence on the measurement result of the sight test can be determined quantitatively.

Diaphragms and/or filters, which are suitable for a further differentiation of the sight test, can be pivoted into the beam path between the imaging device and the deflecting device. Thus, for example, the introduction or withdrawal of diaphragms in the beam path is suitable for measuring the eyes of the subject under test individually or together. However, it is also possible instead for polarization filters to be pivoted into the beam path, if a binocular test is to be place in this way, and which can also be executed as an anaglyph test by means of red/green filters which are pivoted into the beam path. The sight testing apparatus is therefore also suitable for testing spatial vision, horizontal and vertical muscle balance and the fusion (all binocular functions) of the subject under test.

In a simple way, the illumination device can comprise a light source, a collimator, and a diffusing screen being expediently provided to produce diffuse light between the illumination device and the test object. In addition, it is possible for a color conversion filter to be provided between the illumination device and the test object, in order in this way to produce diffuse light of exact wavelength and also be to be able at the same time to test the color sense of the subject under test, using the sight testing apparatus. Even more precisely, disturbances in color vision can be measured if, preferably in the region of the imaging device, color diodes, in particular two-color diodes are provided, are imaged into the eyes of the subject under test, for example together with a single color diode, which emits yellow light and serves as a comparison.

It is possible that the test object is produced by a test disk or test drum, on which a multiplicity of test fields are provided, each of which can be brought as an instantaneous test object into the beam path, said test fields being, for example, equipped for the determination of the resolution capacity with the known optotypes (landoldt rings, letters, numbers or the like). Instead of this, however, the retest object can also be produced electronically, for example, by a monitor or by a panel of liquid crystals; in the case of this construction it is possible to manage without and electromechanical stepping drive such as is needed for the mechanical test disk, and the test object can be produced with the aid of a computer.

The imaging device can comprise a concave mirror and a partly transparent mirror, which is assigned spatially fixed in relation to the concave mirror. In a particularly preferred embodiment, is is instead formed by an achromatic lens system. Such an "achromat" can be implemented much more compactly and can be kept sufficiently wide that one single lens system can be used for both the eyes of the subject under the test.

As already indicated above, the sight testing apparatus according to the invention can be implemented in a particularly advantageous manner if the full deflection device is formed by a (single) half-cube prism, which is then the only functional element, the half-cube prism must be able to be adjusted along the base path of the beam fragments formed thereby. A corresponding adjustment can be undertaken in a simple way by the full deflection device being able to be driven by a threaded spindle which is driven by hand or by a motor and which cooperates with a spindle nut fastened to the full deflection device. Such a spindle drive operates continuously and can be implemented in a simple way in a desired transmission by means of the selection of the pitch of the movement thread used and can be adapted to manual or motor operation. In particular, a motor-driven design is favorable in the case of an arrangement in which, as is still to be explained, the test sequence is carried out largely automatically.

It is expedient if, just as in the case of the imaging device, all remaining optical components located in the beam path are also constructed to be sufficiently wide so that both eyes are involved in the test, even in the case of a large inter-pupil distance of the subject under test, if they are not blanked off individually or together from the beam path by means of one of the diaphragms. This is much simpler than in the case of stereoscopically operating sight testing apparatus in which all the optical functional elements are present twice and must be matched to one another.

The sight testing apparatus can be configured to be particularly simple and user-friendly if the drives of the diaphragms and filters, the test objects and the full deflection device as well as the deflecting device can be actuated from a preferably common electronic control unit for example, under program control, or selectively by means of a hand-operated, wire-free remote control. Such a remote control can be equipped with a display made of liquid crystals for monitoring the instructions entered and which a programming keyboard, so that the operation of the sight testing apparatus does not require any kind of special knowledge for the programming of all tests.

Furthermore, it is possible for the control unit to be linked to a computer. If in this case, just as in the case of remote control, the operating states and parameters of the respective test are indicated, for example by means of a display of liquid crystals or a monitor, the test result can be evaluated very logically in the computer; it is also possible to make the test sequence visible in the monitor via a corresponding program, so that the sight test can be followed conveniently by the tester. Such a mode of operation also serves for the exclusion of test errors; that it is for, for example, no longer possible for the results from the examination of a right eye to be ascribed to the left eye, as can quite possibly occur in the case of a test which is not computer-aided. At the same time, all the other known advantages of computer-aided operation are also available (storage of the data, preparation of the documents from the tests, etc.).

The sight testing apparatus according to the invention is also suitable for direction determination of the stereoscopic visual ability of a subject under test, if a real, secondary test object is arranged in the field of view of the subject under test outside the sight testing apparatus and its distance is compared with that of the image of the primary test object, which is located within the sight testing apparatus. This is carried out in a simple manner by the subject under test adjusting the full deflection device until he or she considers the distance of the primary test object to be equal to the simultaneously perceptible distance of the secondary test object. The difference between the two distances, which can be determined without difficulty in such a test, serves as a pointer to the stereoometric visual ability of the subject under test.

Accordingly, the implementation according to the invention of the sight testing apparatus forms the basis for a device which can be used in a very versatile manner, is easy to operate and is compatible with convenient evaluation of the measurements, which can nevertheless be implemented very compactly and furthermore has all the advantages which are associated with a free-view sight testing apparatus.

BRIEF DESCRIPTION OF THE DRAWINGS

The invention is explained in more detail below, using an exemplary embodiment, with reference to the drawing, in which.

DETAILED DESCRIPTION

Figure 1:
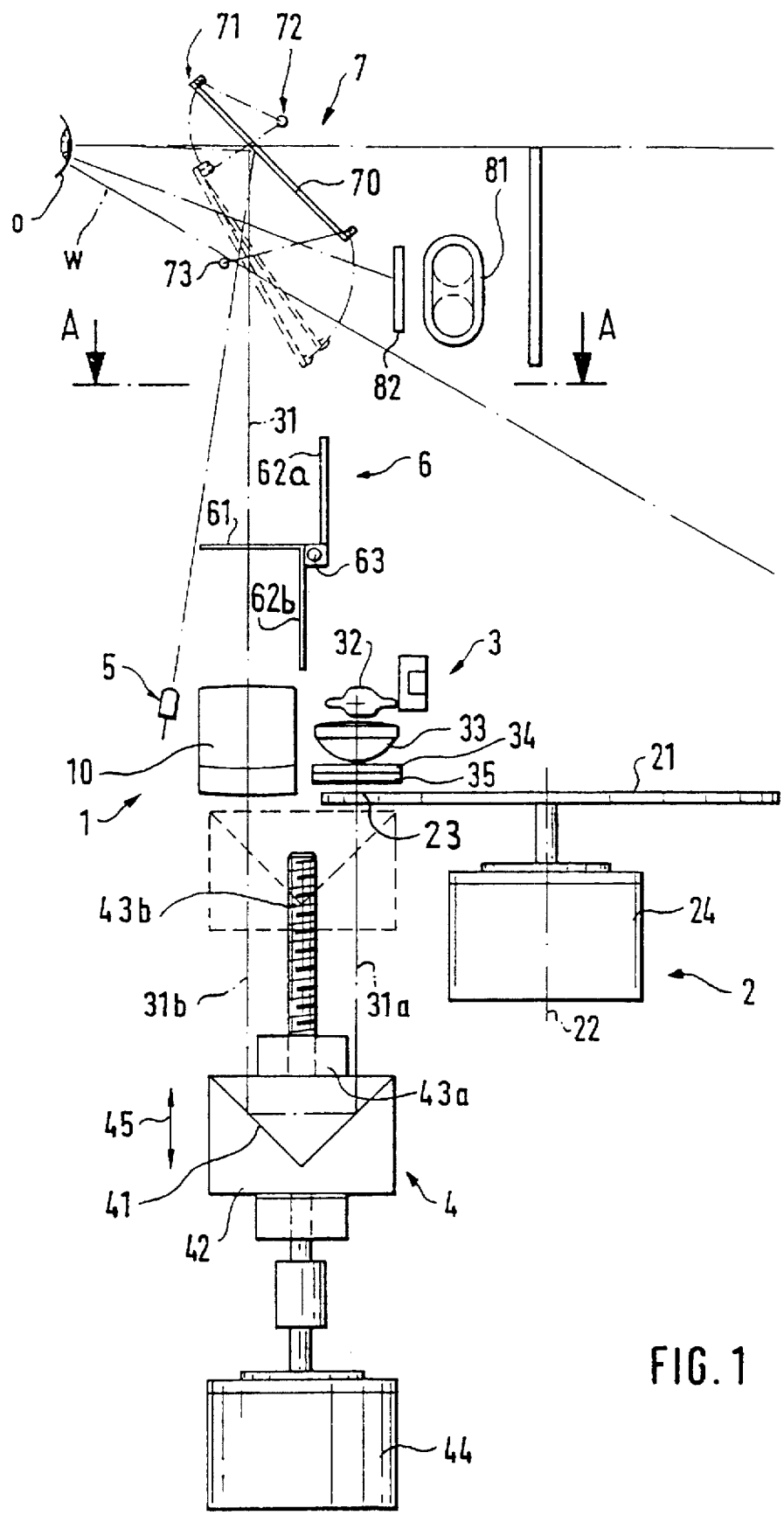
FIG. 1 shows a test embodiment of a sight testing apparatus according to the invention.

A sight testing apparatus according to the invention contains, corresponding to FIG. 1, in a common housing which is left out in the drawing, firstly an imaging device 1, which images a test object in at least one of the eyes O of a subject under test. The test object is in each case provided on a test field 23 of a test field carrier 2 and comprises suitable optotypes which are normal in the discipline; letters, numbers or Landoldt rings are generally used for this.

Figure 2:
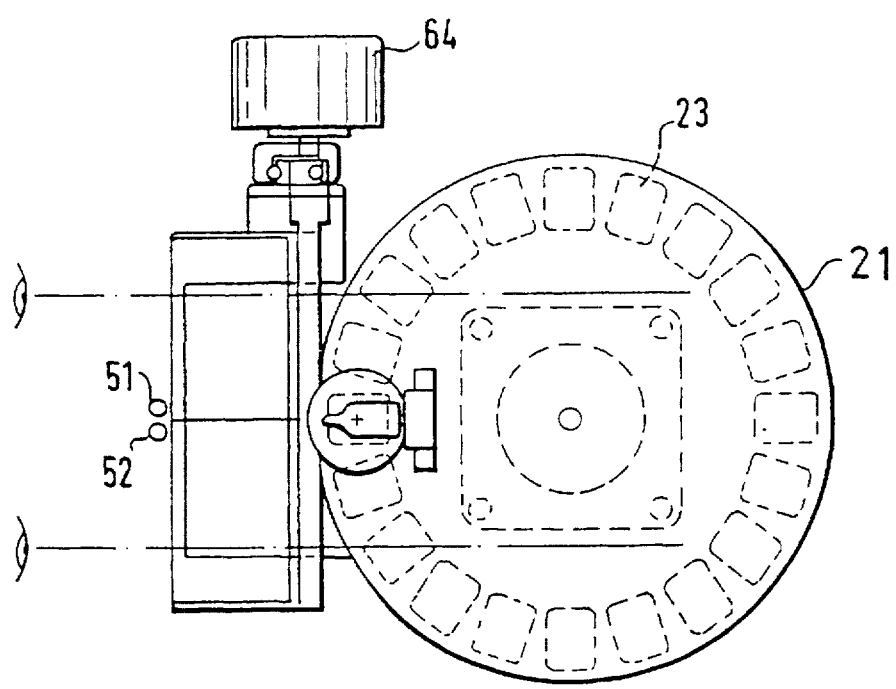
FIG. 2 shows a section A—A from FIG. 1.

The test field carrier 2 has, as essential functional element, a circular-shaped flat test disk 21 which can be rotated about a vertical carrier axis 22 and to whose periphery a multiplicity of test fields 23 are applied. An electric motor drive 24, which is connected to a stepping switch gear or the like, drives the test disk 21 in such a way that (FIG. 2) a desired test field 23 is moved into the beam path 31 of an illumination device 3 and a test object located on the test field 23 is activated for the running test. The drive 24 for selecting the desired test field 23 is in this case switched either manually as required or is driven by a central control unit according to a predetermined program. The entire test field carrier 2 is otherwise fixed in the housing of the sight testing apparatus.

The illumination device 3, which is likewise fixed in the housing, fitted just above the test disk 21, produces a beam path 31, which is parallel to the carrier axis 22, through the adjacent respective test field 23. It essentially comprises a light source 32 formed by a halogen lamp, whose light is formatted in the desired way in a subsequent collimator 33. A diffusing screen 34 placed downstream of the collimator 33 ensures that an illumination device 3 is produced which emits uniformly diffuse light. A color conversion filter 35 produces a specific color temperature, for example always constant daylight, in order to secure unchanging conditions during the use of test charts during a color test. An annoying ultraviolet component can be removed from the light by means of a surface purposeful filter; however it is also possible to achieve the same effect with a blocking layer, which is vapor-deposited onto the color conversion filter 35, for the ultraviolet light.

The beam path 31 is fully deflected through 180° (upward) in a full deflection device 4. For this purpose, flat surfaces 41 are provided which are reflective, are inclined at 90° with respect to each other and at 45° with respect to the incident or emergent beam path 31 and, in the exemplary embodiment, are a component part of a half-cube prism 42, but can also be provided simply from correspondingly oriented flat mirrors which replace the half-cube prism 42. In this way, the beam path 31 from the illumination device 3 is decomposed into the imaging direction 1 into two parallel beam path fragments 31a, 31b which run in opposite directions.

The full deflection device 4 can be displaced in the vertical direction by means of a spindle drive 43; for this purpose, a spindle nut 43a is connected to the half-cube prism 42 and, together with a threaded spindle 43b which is supported in a fixed position in the housing of the sight testing apparatus, forms the spindle drive 43 which can be actuated either by hand or, as in FIG. 1, by an electric drive 44. A directional arrow 45 indicates the direction of motion of the full deflection device 4; the position of the full deflection prism 42 drawing with a continuous line and the position of the full deflection prism 42 drawn with a dashed line illustrate the two possible end positions.

In this case, exactly like the drive 24 for selecting the desired test field 23, the drive 44 is either switched on manually as required or is driven by a central control unit in accordance with a predetermined program. The entire full deflection device 4, apart from the half-cube prism 42 and the spindle nut 43a connected to the latter, is once more provided in a fixed position in the housing of the sight testing apparatus.

Used as imaging device 1 for the test object illuminated by the beam path 31 is a color-corrected lens system 10 which can be kept very compact in terms of its construction and can be passed through by the beam path 31 without deflection. It images the image, transported using the beam path 31, of the test object into the eyes O of the subject under test, since the length of the optical path W from the imaging device 1 as far as the eyes O is equal to the (single) focal length of the imaging device 1. The sharpness of the image is in this arrangement independent of the instantaneous position of the full deflection device 4, so that the image of the test object in the adjustment range of the full deflection device 4 is always presented with the same sharpness.

Directly adjacent to the imaging device 1 there are provided a two-color diode 51 (red/green) and a single-color diode 52 (yellow), whose light can be switched into the eyes O of the subject under test. The light-emitting diode system 5 can be used for the purpose of measuring the normalcy of color vision of the eyes O, but also serves as a reference plane in order to test the spatial visual capacity.

In this case, the subject under the test has the task of setting the test object in such a way (for example by means of an advance and withdrawn key) that the test object is located for him or her exactly in the reference plane. By means of a computational process, the stereoscopic angle set can be specified precisely to angular seconds.

To examine binocular vision, polarization filters 61 can optionally be pivoted an analyzers into the beam path 31. The corresponding test objects on the test disk for examining the spatial vision, the horizontal or vertical muscle balance and the fusion capability are correspondingly polarized, for example as a result of negative or positive polarization processes.

The polarization filters 61 can optionally also be replaced by red/green filters, the binocular tests must then accordingly be laid out on the red/green test field, in order to test in accordance with the anaglyph process.

The polarization filters 61 are arranged on a diaphragm wheel. For instance, this diaphragm wheel 6 is implemented in such a way that it can lock every 90°. Hence, diagraphms 62, 62b can optionally be pivoted in front so that in each case the right or the left visual channel can be covered, in order to be able to be examine also in a monocular fashion.

In a further position, rotated through 90°, the visual channel for both eyes is exposed without filters. This diaphragm wheel does not need to be located directly in front of the eyes of the subject under test but can be arranged at a suitable location in the apparatus. It is thus difficult for malingerers to detect direction in each case whether it is just the right eye, the left eye or both eyes that are being tested.

Exactly like the filter system 6, a deflecting device 7 can be pivoted about a horizontal axis which, however, is not designed here as an ideal axis. The pivotable and partly transparent deflecting device 7 comprises in a simple way a flat beam-splitting mirror which is set obliquely and partly reflects and can partly be passed through uninterrupted by the beam path 31 deflected thereby, the horizontal borders 71 of said beam-splitting mirror in each case each being pivotable about an axis, real axis 72, 73, fixed in the housing.

The deflecting device 7 is essentially pivotable into three positions indicated in FIG. 1, in which it can in each case expediently be locked by a latch, so that the positions can be conveniently positioned in the case of pivoting the beam-splitting mirror 70 by hand. In a first position, drawn with a continuous line, in which the beam-splitting mirror 70 is located at 45° to the horizontal, the subject under test can freely observe the test object against the background of the real testing room in the horizontal viewing direction; in this way, for example, the far-sightedness of the subject under test can be tested in a simple way. In a second and a third position, in each case drawn with a dashed line, of the beam-splitting mirror 70, the subject under test has to inclined his or her view whilst maintaining an unchanged head position, in order to detect the test object, so that near-sightedness can also be measured. In this arrangement, the beam-splitting mirror 70 can be positioned in such a way that the beam path 31 is direction from the eyes O to a direct light source 81 which is accordingly imaged in addition to the test object in the eyes O and allows measurements also under defined contrast conditions. A diffusing screen 82 ensures that the background appears illuminated diffusely.

The sight testing apparatus according to the invention can be operated both manually and by means of an electronic control device, left out of the drawing, suitable or carrying out program-controlled tests. In each case, the control can be undertaken from an LCD-aided remote control. The details of this lie outside the invention and are therefore not explained further.

Figure 3:
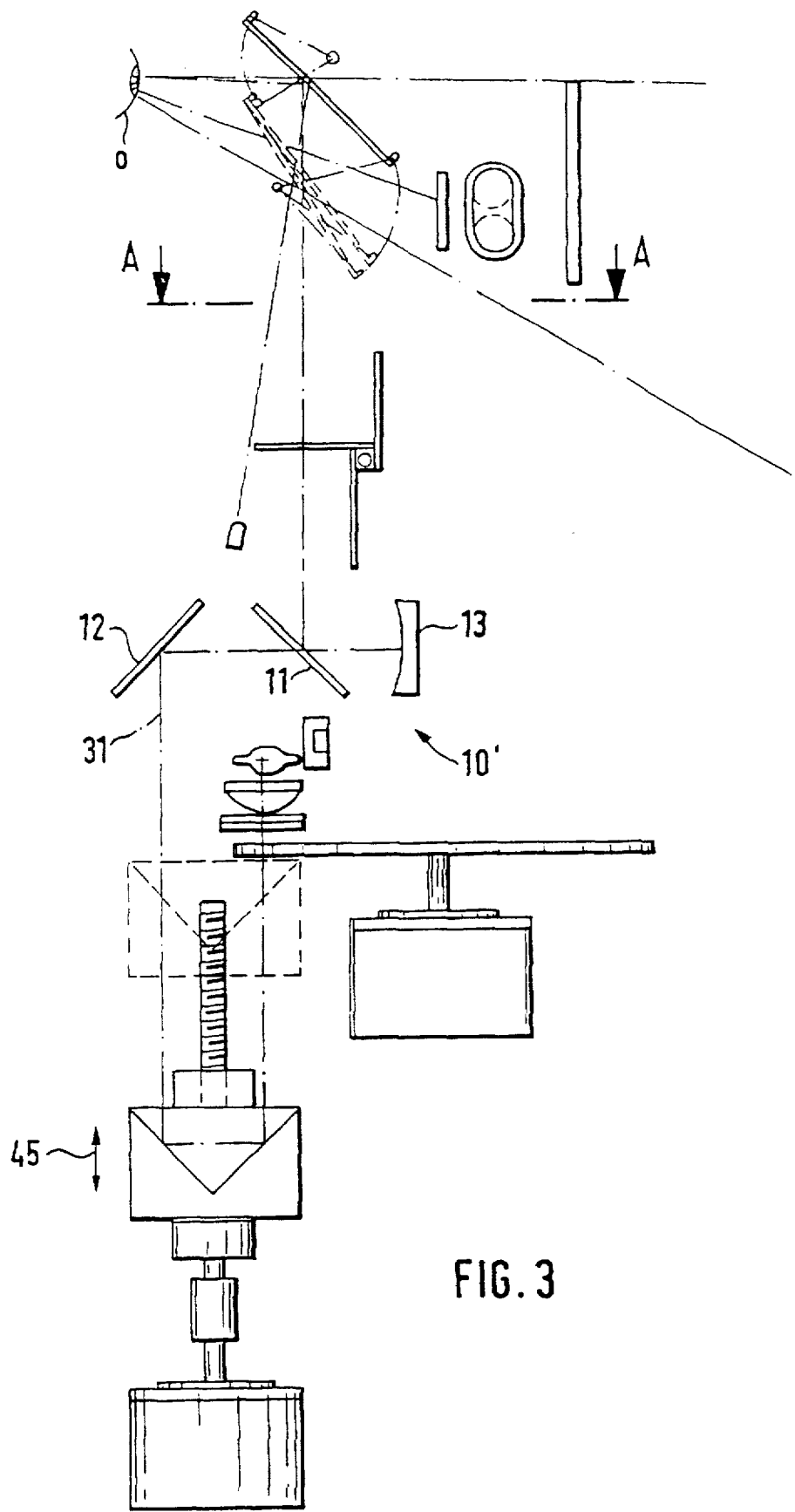
FIG. 3 shows a further embodiment of the sight testing apparatus corresponding to FIG. 1, all in a schematically simplified representation.

In FIG. 3, the lens system 10 has been replaced by a mirror system 10', which comprises a partly transparent, flat mirror 11 and a concave mirror 13, in whose focal plane once more the eyes O are provided. A further, totally reflecting mirror 12 directs the beam path 31 coming from the full deflection device 4 into the concave mirror 13. Both flat mirrors 11, 12 are installed in a fixed position, inclined at 45°, in the housing of the sight testing apparatus, as is the concave mirror 13. Otherwise, the arrangement of FIG. 3 corresponds to that of the embodiment according to FIGS. 1 and 2.

The sight testing apparatus in the embodiment described can also be used as a visual character projector. In this case, the apparatus is set up in front of a, for example motor-controlled, photopter, that is to say an apparatus in which the correction lenses are switched in front of the patient's eye via stepping motors. In this combination of apparatus, it is possible to carry out to the determination of eyeglasses at a distance, but also close to and in all intermediate areas. As a result of the optics, it is not absolutely necessary to have a 5 m room, which at the moment must be the case when using a conventional projector.

The polarization filters and the monocular covering diaphragms can be dispensed with in the sight testing apparatus in combination with a photopter, since these functions are already contained in the photopter.

The embodiments of the invention in which an exclusive property or privilege is claimed are defined as follows:

1. A sight testing apparatus with a free through-view, comprising:
 an illumination device creating a beam path for testing an eye of a patient;
 a test object fixed in the beam path and being one of a test disk and test drum, each of the test disk and test drum having a plurality of test fields, one of the test fields being positioned in the beam path for sight testing, each of the test fields being interchangeable in the beam path;
 an imaging device for the virtual imaging of the test object into an eye of a patient, the test object being located at the focus of the imaging device and within the focal length of the imaging device and being imaged at different distances into an eye of a patient;
 an optical full deflection device provided in the beam path between the imaging device and the test object for deflecting the beam path through 180°, the full deflection device defining two parallel elongate fragments of the beam path, the full deflection device being displaceable along the longitudinal direction of the two beam path fragments, the test object being longitudinally immovable relative to the two beam path fragments; and
 the imaging device and the full deflection device being sufficiently wide to test both eyes of a patient regardless of interpupil distance of the patient.

2. The sight testing apparatus according to claim 1, wherein the test object is a fixed illumination device.

3. The sight testing apparatus according to claim 1, wherein a partly transparent second deflecting device is provided in the beam path between an eye of the patient and the imaging device.

4. The sight testing apparatus according to claim 3, wherein the second deflecting device alters the viewing direction of the eye and is pivotable in the beam path.

5. The sight testing apparatus according to claim 4, wherein the second deflecting device is selectively fixable in at least two pivotally offset positions.

6. The sight testing apparatus according to claim 5, wherein a viewing direction of the patient extends horizontally, and the second deflecting device is positioned in the viewing direction and is locked in one of the at least two positions partially reflecting the viewing direction along the beam path onto the full deflection device and hence the test object testing patient vision of the patient.

7. The sight testing apparatus according to claim 5, wherein a viewing direction of the patient extends declined with respect to horizontal, and the second deflecting device is locked in one of the at least two positions reflecting the viewing direction onto the test object testing near vision of the patient.

8. The sight testing apparatus according to claim 3, wherein the second deflecting device is a partly transparent flat beam-splitting mirror.

9. The sight testing apparatus according to claim 8, wherein a further test object is provided, a diffuse direct light source is provided in a fixed position creating a second beam path imaging the further test object into an eye, and the second deflecting device is positioned so that the second beam path extends undeflected through the second deflecting device passing light from the direct light source together with an image of the further test object into the eye of the patient.

10. The sight testing apparatus according to claim 3, wherein at least one of diaphragms and filters are pivotable into the beam path between the imaging device and the second deflecting device.

11. The sight testing apparatus according to claim 10, wherein a plurality of drives respectively position the diaphragms, the filters, the test objects, the full deflection device, and the second deflecting device, and an electronic control unit controls the plurality of drives.

12. The sight testing apparatus according to claim 11, wherein the drives are actuated by one of a program control and a hand-operated, wire-free remote control.

13. The sight testing apparatus according to claim 12, wherein one of a liquid crystal display and a monitor displays positioning of the drives and parameters of a respective sight test.

14. The sight testing apparatus according to claim 11, wherein the control unit is linked to a computer.

15. The sight testing apparatus according to claim 1, wherein the illumination device comprises a light source and a collimator.

16. The sight testing apparatus according to claim 15, wherein a diffusing screen is positioned between the illumination device and the test object.

17. The sight testing apparatus according to claim 15, wherein a color conversion filter is positioned between the illumination device and the test object.

18. The sight testing apparatus according to claim 1, wherein the imaging device is an achromatic lens system.

19. The sight testing apparatus according to claim 1, wherein the imaging device comprises a concave mirror and a partly transparent mirror.

20. The sight testing apparatus according to claim 1, wherein the full deflection device is a half-cube prism.

21. The sight testing apparatus according to claim 1, wherein a threaded spindle driveably positions the full deflection device, the threaded spindle being driven by one of hand and a motor, and a spindle nut fastened to the full deflection device is engaged on the threaded spindle.

22. The sight testing apparatus according to claim 1, wherein color diodes are provided adjacent the imaging device, the color diodes image select colors into the eyes of a patient.

23. The sight testing apparatus according to claim 1, wherein a real, secondary test object is arranged in the field of view of the patient outside the sight testing apparatus, and a distance of the secondary test object from the patient is compared with that of the image of the test object which is located within the sight testing apparatus.

24. A sight testing apparatus with a free through view, comprising:
   a test object being produced electronically by one of a monitor and a liquid crystal display, each of the monitor and liquid crystal display being adpated to produce a plurality of the test objects and one test object being transmitted along a beam path to an eye of a patient for sight testing;
   an imaing device for the virtual imaging of the test object into an eye of a patient, the test object being located at the focus of the imaging device and within the focal length of the imaging device and being imaged at different distances into an eye of a patient;
   an optical full deflection device provided in the beam path between the imaging device and the test object for deflecting the beam path through 180°, the full deflection device defining two parallel fragments of the beam path, the full deflection device being displaceable in the direction of the two beam path fragments, the test object being immovable relative to the two beam path fragments; and
   the imaging device and the full deflection device being sufficiently wide to test both eyes of a patient regardless of interpupil distance of the patient.

25. A sight testing apparatus, comprising:
   an illumination device creating a light path for testing an eye of a patient;
   a test object positioned in the light path and having means for producing a plurality of exchangeable test fields, one of the test fields being selected to test an eye of a patient and directly positioned in the light path, the test object being longitudinally fixed in the light path;
   an imaging device for imaing the test object into an eye of a patient positioned along the light path, the one test field of the test object being located within the focal length of the imaging device and being imaged at different distances to an eye of a patient;
   an optical full deflection device adjustably positioned in the light path between the test object and the imaging device, the full deflection device deflecting the light path through 180° and thereby separating the beam path into adjacent parallel first and second beam segments, the first beam segment extending between the test object and the full deflection device, the first beam segment being lengthened by adjusting a position of the deflection device, the second beam segment extending between the deflection device and the eye of a patient through the imaging device; and
   the test object, the imaging device, and the deflection device all having sufficient width so that both eyes of a patient are tested.

* * * * *

UNITED STATES PATENT AND TRADEMARK OFFICE
CERTIFICATE OF CORRECTION

PATENT NO. : 5,793,469

DATED : August 11, 1998

INVENTOR(S) : Carsten FEIERTAG et al

It is certified that error appears in the above-indentified patent and that said Letters Patent is hereby corrected as shown below:

Column 8, line 40; change the first occurrence of "patient" to ---distant---.

Signed and Sealed this

First Day of December, 1998

*Attest:*

BRUCE LEHMAN

*Attesting Officer*  *Commissioner of Patents and Trademarks*